US008617043B2

(12) United States Patent
Ten Eyck et al.

(10) Patent No.: US 8,617,043 B2
(45) Date of Patent: *Dec. 31, 2013

(54) SYSTEM AND METHOD OF MONITORING THE PHYSIOLOGICAL CONDITION OF AN INFANT

(75) Inventors: Lawrence G. Ten Eyck, Ellicott City, MD (US); Aparna Katakam, Silver Spring, MD (US); Karen Starr, Monkton, MD (US)

(73) Assignee: General Electric Company, Schenectady, NY (US)

( * ) Notice: Subject to any disclaimer, the term of this patent is extended or adjusted under 35 U.S.C. 154(b) by 266 days.

This patent is subject to a terminal disclaimer.

(21) Appl. No.: 12/970,235

(22) Filed: Dec. 16, 2010

(65) Prior Publication Data

US 2012/0157757 A1 Jun. 21, 2012

(51) Int. Cl.
*A61G 11/00* (2006.01)

(52) U.S. Cl.
USPC ............................................. 600/22

(58) Field of Classification Search
USPC ................ 600/21, 22, 595; 128/897–899
See application file for complete search history.

(56) References Cited

U.S. PATENT DOCUMENTS

| 4,936,824 | A | 6/1990 | Koch et al. |
| 5,474,517 | A | 12/1995 | Falk et al. |
| 6,213,935 | B1 | 4/2001 | Mackin et al. |
| 6,409,654 | B1 | 6/2002 | McClain |
| 7,038,588 | B2 * | 5/2006 | Boone et al. ............... 340/573.1 |
| 7,282,022 | B2 | 10/2007 | Falk et al. |
| 8,081,082 | B2 * | 12/2011 | Malik et al. ............... 340/573.1 |
| 2008/0077020 | A1 | 3/2008 | Young et al. |
| 2010/0030122 | A1 * | 2/2010 | Gaspard ....................... 601/136 |

FOREIGN PATENT DOCUMENTS

| EP | 1579801 A1 | 9/2005 |
| EP | 1683482 A1 | 7/2006 |
| SU | 1690751 A1 | 11/1991 |
| WO | 9726824 A1 | 7/1997 |
| WO | 0004828 A1 | 2/2000 |
| WO | 02062282 A1 | 8/2002 |
| WO | 2006104480 A1 | 10/2006 |
| WO | 2012082297 A2 | 6/2012 |

OTHER PUBLICATIONS

Search Report and Written Opinion from corresponding PCT Application No. PCT/US2011/061104 dated Aug. 7, 2012.

(Continued)

*Primary Examiner* — Charles A Marmor, II
*Assistant Examiner* — Shannon McBride

(57) ABSTRACT

A system for monitoring the physiological conditions of an infant includes an infant microenvironment. A motion sensor is disposed about the microenvironment. A processor is communicatively connected to the motion sensor. The processor receives motion signals from the motion sensors and processes the motion signals to derive an indication of a stress level of the infant. A method of monitoring the physiological condition of an infant includes detecting motion of the infant with motion sensors. A baseline motion for the infant is derived from the detected motion with a processor. An onset or change in at least one auxiliary parameter is monitored with an auxiliary sensor. Motion of the infant is monitored with the motion sensor after the onset or change in the at least one auxiliary parameter. A stress level of the infant is derived with the processor from the monitored motion of the infant.

8 Claims, 5 Drawing Sheets

(56) References Cited

OTHER PUBLICATIONS

Invitation to Pay Additional Fees from corresponding PCT Application No. PCT/US2011/061104 dated Mar. 6, 2012.

Search Report from GB Application No. 1216829.0 dated Jan. 17, 2013.

Magnavita, V. et al., "Noise exposure in neonatal intensive care units", Acta Otorhinlaryngol Ital, 1994, vol. 14, No. 5, p. 489-501.

* cited by examiner

US 8,617,043 B2

SYSTEM AND METHOD OF MONITORING THE PHYSIOLOGICAL CONDITION OF AN INFANT

BACKGROUND

The present disclosure relates to the field of infant monitoring. More specifically, the present disclosure relates to monitoring stress indicators in neonates.

Stress is physiologically undesirable in neonates. Increased stress levels cause the neonate to consume extra calories to generate stress responses. This consumption of extra calories diverts caloric consumption from basal and developmental efforts that are critical to the survival of the neonate.

The detection of neonate physiological conditions with respect to stress responses can provide clinicians with an additional diagnostic tool, resulting in directed clinician interventions or responses.

BRIEF DISCLOSURE

A system for monitoring the physiological condition of an infant includes an infant microenvironment defined by a horizontal surface and at least one wall. A motion sensor is disposed about the microenvironment. A processor is communicatively connected to the motion sensor. The processor receives motion signals from the motion sensor and processes the motion signals to derive an indication of a stress level of the infant.

A method of monitoring the physiological condition of an infant includes placing an infant within a microenvironment monitored by a plurality of motion sensors. A motion of the infant is detected with the motion sensors. A baseline motion is derived for the infant. An onset or change in at least one auxiliary parameter is monitored. Motion of the infant with respect to the baseline motion is monitored after the detected onset or change in the at least one auxiliary parameter. A processor derives an indication of a stress level of the infant from the monitored motion of the infant.

A system for monitoring a condition of a plurality of infants in an infant care facility includes a plurality of infant care stations. Each infant care station includes a microenvironment, a motion sensor, an environmental sensor, and a processor. A central processor is communicatively connected to each of the infant care stations. The central processor compares the environmental sensor signals from each of the infant care stations and determines correlations between environmental conditions experienced in each of the infant care stations and corresponding indications of the stress level of the infants.

DETAILED DISCLOSURE

Figure 1:
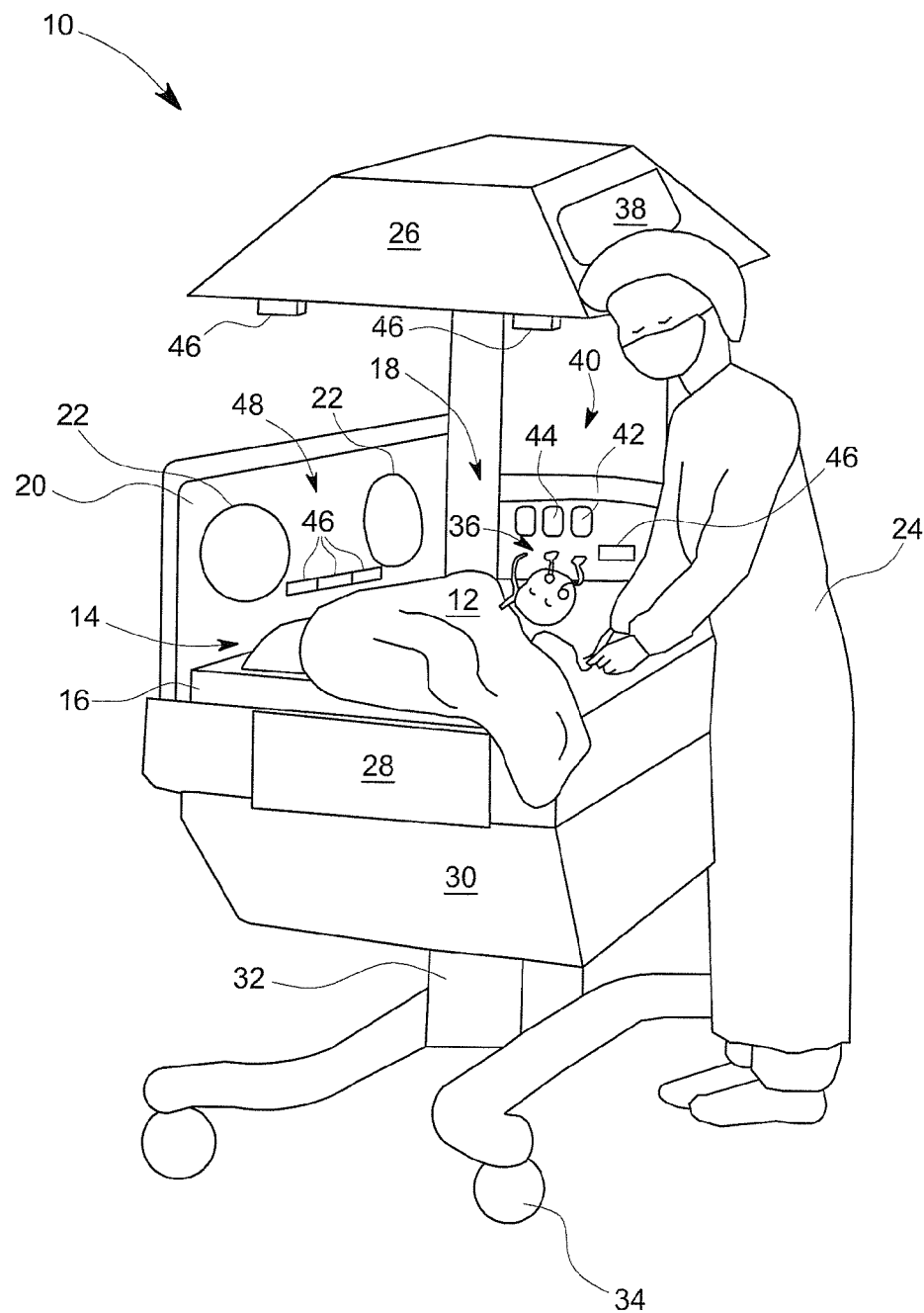
FIG. 1 is an environmental view of an embodiment of a system for monitoring the physiological condition of an infant.

FIG. 1 depicts an embodiment of a system 10 for monitoring the physiological condition of an infant 12. An infant care station 14 includes a generally horizontal surface 16 upon which the infant is supported. A microenvironment 18, within which the infant 12 is disposed, is at least partially defined by the horizontal surface 16 and at least one wall 20. The at least one wall 20 may be movable or otherwise may include arm ports 22. The movable wall 20 or the arm ports 22 provide a clinician 24 with access to the infant 12.

The infant care station 14 as described and depicted exemplarily herein is a combined infant care station with a movable canopy as will be disclosed in greater detail. One example of this infant care station 14 is the OmniBed, available from General Electric Company. However, it is to be understood that in alternative embodiments, the infant care station 14 may be any of a variety of infant care station constructions, including, but not limited to, incubators, radiant warmers, and bassinets. Embodiments of each of these infant care stations define a microenvironment for an infant with at least a generally horizontal surface and a wall.

The microenvironment 18 is regulated by the infant care station 14 to control environmental conditions such as temperature and medical gas concentration within the microenvironment 18. One common environmental condition that is controlled in the infant care station 14 is the temperature. The temperature of the microenvironment 18, and the infant 12, is controlled in one or a combination of manners. A canopy 26 is vertically adjustable with respect to the infant 12 and the horizontal surface 16. The canopy 26 includes a radiant heater that projects heat downward onto the infant 12 and the horizontal surface 16. A convective heater 28 is disposed within a base 30 of the infant care station 14. The convective heater 28 draws in ambient air, heats the ambient air with a heating coil (not depicted) or other heating element and blows the heated air into the microenvironment 18.

The infant care station 14 includes an adjustable pedestal 32 that causes the horizontal surface 16 to be vertically adjusted. The infant care station 14 further includes casters 34. This makes the infant care station 14 mobile, such that an infant care station 14 may be moved to a desired location for receiving and treating an infant. Alternatively, the infant care station 14 may be used to move the infant 12 from one location to another.

The infant care station 14 includes a variety of sensors and outputs that facilitate the care and treatment of the infant 12 by the clinician 24. In an exemplary embodiment, the infant care station 14 includes one or more physiological transducers 36. The physiological transducers 36 acquire physiological parameters from the infant 12. The physiological parameters acquired by the physiological transducers 36 may be biopotentials such as, but not limited to, electrocardiograph (ECG), electromyograph (EMG), and electroencephalograph (EEG). Alternatively, the physiological parameters obtained by the physiological transducers may be other types of physiological values such as oxygen saturation (SPO2) or non-invasively obtained blood pressure (NIBP). It is understood that other physiological parameters may be obtained by the physiological transducers 36, as would be recognized by one of ordinary skill in the art.

The infant care station 14 processes the physiological parameters obtained by the physiological transducers 36 and presents physiological values to the clinician 24 on a graphical display 38. The graphical display 38 is exemplarily shown as being part of, or integrated with, the canopy 26; however, it is to be understood that a variety of graphical displays 38 and display locations may be used in the infant care station 14, as would be recognized by one of ordinary skill in the art.

Embodiments of the system 10 include one or more environmental sensors 40. Examples of the environmental sensors 40 are a sound sensor 42 and a light sensor 44. The sound sensor 42 measures ambient sound within the microenvironment 18. In an embodiment, the sound sensor 42 measures the sound level in decibels. The sound picked up by the sound sensor may be due to the mechanical operation of the infant care station 14, the intervention by the clinician 24, or from ambient sound external to the infant care station 14.

The light sensor 44 detects the ambient light in the microenvironment 18 and measures luminescence in lumens. The light detected by the light sensor 44 may be due to one or more external apparatus (not depicted) that are used in conjunction with the infant care station 14 for monitoring or treating the condition of the infant 12. Alternatively, the ambient light in the microenvironment 18 monitored by the light sensor 44 is from light sources outside of the infant care station 14. Additionally, some embodiments of the canopy 26 include one or more lights (not depicted) that may be actuated by the clinician 24 in order to specifically provide increased illumination of the infant 12. All of these sources of light and other are picked up and registered by the light sensor 44.

The system 10 further includes a plurality of motion sensors 46. The motion sensors 46 may be any of a variety of motion sensing implementations. A first non-limiting example of a motion sensor 46 is a digital video capture device, such as a video camera. In a more specific embodiment, the video camera is a charge coupled device (CCD) and may operate in one or more of the visible light, ultraviolet light, or infrared light spectrums. In an alternative embodiment, the motion sensor 46 projects a beam, such as a laser, and receives the beam with an optical transducer (not depicted) opposite the motion sensor 46 wherein the breaking of the beam is detected as no signal is obtained by the optical transducer. In a still further embodiment, the motion sensor 46 "paints" the subject with electromagnetic energy, such as a laser, and receives the reflected electromagnetic energy off of the infant 12. This reflection is used to determine the position of the infant 12.

In embodiments of the system 10, a plurality of motion sensors are disposed about the microenvironment 18. As exemplarily depicted in FIG. 1, a plurality of motion sensors 46 may be arranged in a motion sensor array 48. Array 48, in embodiments, extend along the length of the infant 12 or the horizontal surface 16. Alternatively, motion sensors 46 may be arranged in the canopy 26 and directed downwards at the microenvironment 18 and the infant 12.

It will be noted that the number of motion sensors 46 used will depend in part on the specific motion sensing technology used. For example, if the motion sensor 46 is a video camera, embodiments may only require a single camera. Alternatively laser or other electromagnetic energy based motion sensors may require a plurality of sensors to detect a variety of infant movements.

Figure 2:
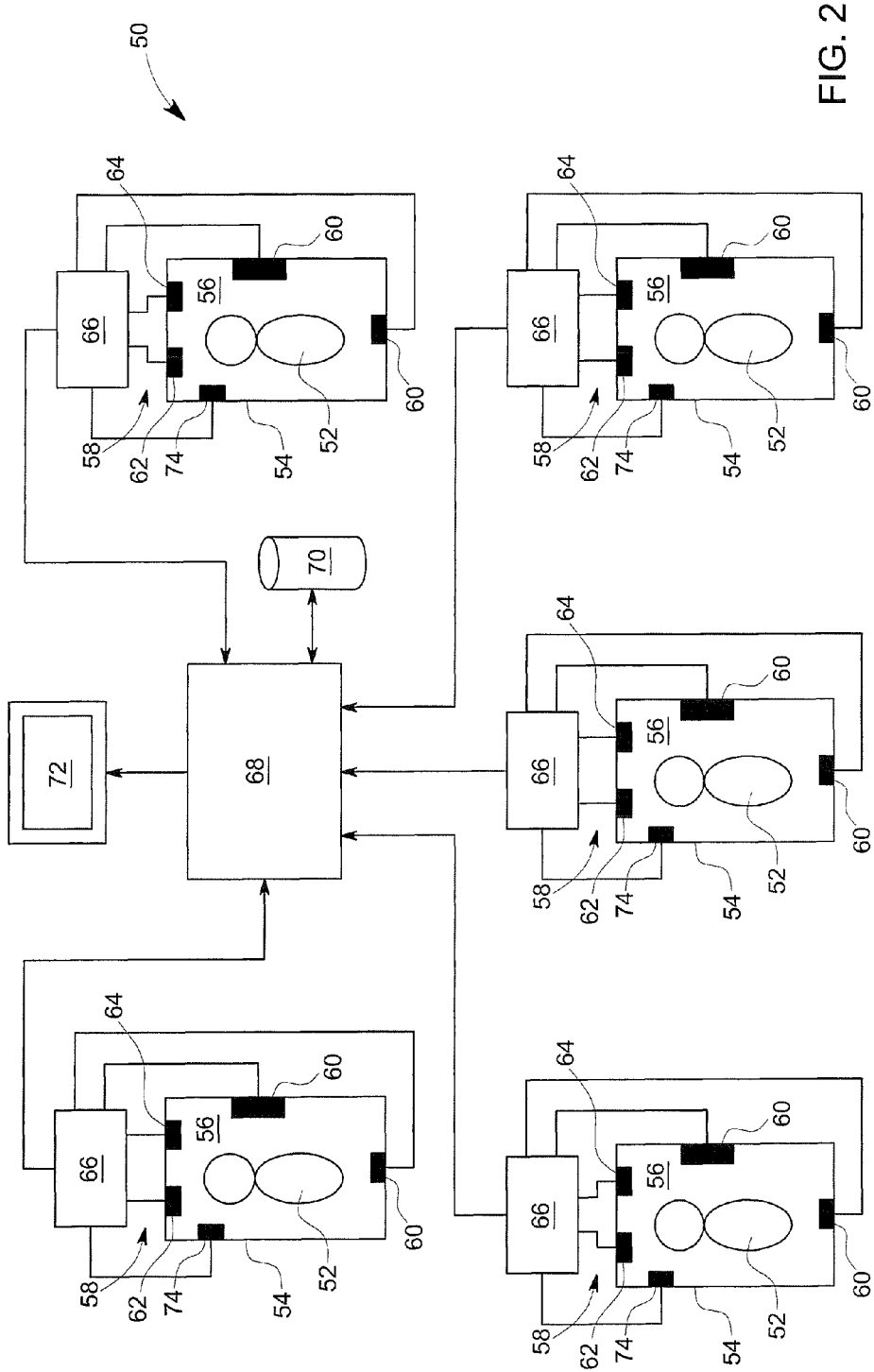
FIG. 2 is a schematic diagram of an embodiment of a system for monitoring a condition of a plurality of infants.

FIG. 2 depicts an embodiment of system 50 for monitoring a condition of a plurality of infants 52. Each infant 52 of the plurality is held within an infant care apparatus 54. The infant care apparatus 54 may exemplarily be the infant care station 14 as described with reference to FIG. 1.

The infant care apparatus 54 defines a microenvironment 56 about the infant 52. The infant care apparatus 54 each further include at least one environmental sensor 56 and at least one motion sensor 58 disposed about the microenvironment 56. Embodiments of the at least one environmental sensor 58 may include one of, or a combination of both a light sensor 62 and a sound sensor 64. The light sensor 62 and the sound sensor 64 may be similar to those as described above with respect to FIG. 1. The at least one environmental sensor 58 monitors an environmental condition of the microenvironment 56, exemplarily the luminescence in the microenvironment 56 or the sound level in the microenvironment 56. The at least one motion sensor 60 detects motion of the infant 52 within the microenvironment 56. In still further embodiments, the at least one motion sensor 60 can further detect the motion of a clinician during the course of an intervention with the infant 52 within the microenvironment 56. Such an intervention may be to adjust, treat, or evaluate the infant 52.

The outputs from the environmental sensor 58 and the motion sensor 60 are provided to a processor 66 that is a component of the infant care station 54. The processor 66 receives the signals from the at least one environmental sensor 58 and at least one motion sensor 60 and performs initial signal processing on the received signals. The processor 66 may operate a graphical display (not depicted) to locally present the detected environmental condition and motion of the infant within the microenvironment 56. An example of such a display is provided in more detail with respect to FIG. 1.

Each of the processors 66 of the infant care stations 54 provides the monitored environmental conditions and infant motion to a central processor 68. The central processor 68 is communicatively connected to each of the processors 66 of the infant care stations 54. In an exemplary embodiment of the system 50, the central processor 68 is a hospital information server that is communicatively connected to each of the infant care stations 54 through a hospital internet. In that embodiment, each of the infant care stations 54 may be located in the same room, such as a neonatal ward or a neonatal intensive care unit (NICU). Each of the infant care stations 54 may communicate with the hospital internet and the central processor 68 through wired or wireless communication connections. In a still further embodiment, infant care stations 54 are remotely located from each other and transmit the monitored environmental condition and infant motion to the central processor 68 through the Internet.

The central processor 68 is further communicatively connected to a computer readable medium 70. In an exemplary embodiment, the computer readable medium 70 is a read only memory (ROM) such as FLASH memory; however, a person of ordinary skill in the art would recognize that alternative forms of computer readable mediums may be used within the scope of the present disclosure.

The computer readable medium 70 is programmed with computer readable code that is executed by the central processor 68 that causes the central processor 68 to operate in the manner as disclosed herein. In an alternative embodiment, the computer readable medium 70 is an integral part with the central processor 68, rather than a separate component communicatively connected to the central processor 68.

The central processor 68 operates to receive the signals from the environmental sensors 58 and the signals from the motion sensor 60 as acquired by each of the processors 66. The central processor analyzes the received environmental sensor signals and motion sensor signals from each of the infant care stations 54 in a comparative manner. This cross to infant analysis provides additional information regarding the environmental conditions experienced and each of the infant care stations 54, and the resulting stress level of each of the infants 52 at the infant care stations 54. The central processor 68 determines correlations between the environmental condition and the infant stress levels.

In an exemplary embodiment, the environmental sensor signals indicate environmental changes that are associated with a clinician interaction with one of the infants 52. These environmental changes may include turning on the lights of the NICU or causing noise within the NICU. The light and noise changes may cause increased stress levels in others of the infants in the NICU that are not receiving intervention. The identification of this residual increases in stress level of the infants 52 not receiving clinician intervention may prompt a change in procedures for clinician interventions in an effort to reduce the stress levels experienced by the other infants 52.

In an alternative embodiment, the infant care stations 54 in the system 50 may be physically located in a plurality of rooms. The environmental sensor signal and the infant stress levels can be compared between the infants 52 in the different rooms in an effort to identify indications of environmental conditions within one of the rooms that result in greater infant stress. With the identification of these exasperatory environmental conditions, clinician efforts may be made to reduce the effects or existence of these conditions and therefore reduce the stress levels of infants in a particular room.

The central processor 68 is communicatively connected to and operates graphical display 72. The graphical display presents the received environmental conditions and infant stress levels. The graphical display 72 is further operated to present the determined correlation between the environmental conditions and the infant stress levels.

In an alternative embodiment of the system 50, each of the infant care stations 54 further include one or more physiological sensors 74. The physiological sensors 74 obtain physiological data from the infant 52. The physiological data may be any of a variety of known physiological data including, but not limited to, biopotentials, SPO2, NIBP, or respiration rate. In this exemplary embodiment, the central processor 68 receives the physiological sensor signals from each of the processors 66 of the infant care stations 54 and the physiological sensor signals are further used in determining infant stress levels.

Figure 3A:
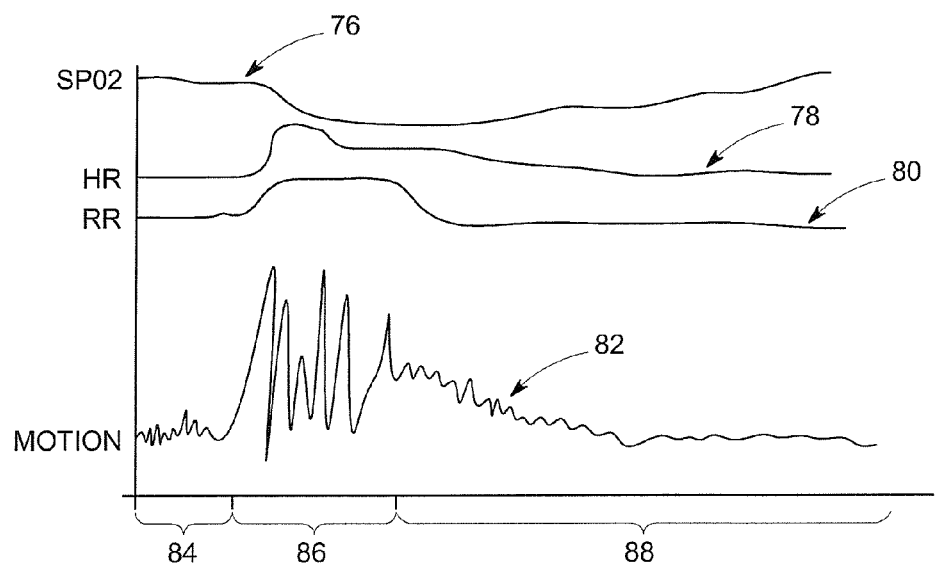
FIGS. 3A and 3B are exemplary graphs of detected motion and monitored physiological parameters.
Figure 3B:
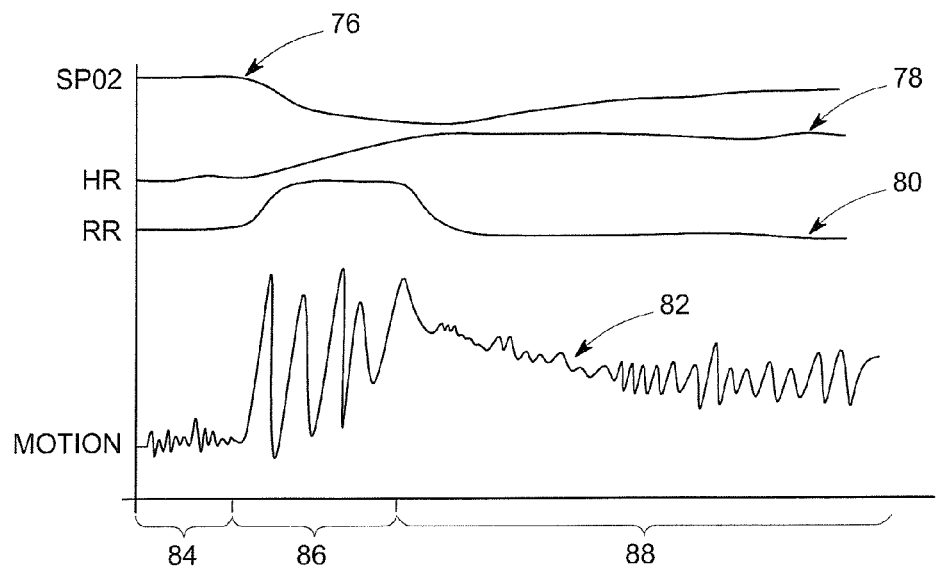

FIGS. 3A and 3B depict exemplary graphs of physiological and motion sensor signals. FIGS. 3A and 3B both include an SPO2 graph 76, a heart rate graph 78, and a respiration rate graph 80. Additionally, FIGS. 3A and 3B include a graph of detected motion intensity 82.

FIGS. 3A and 3B depict two different infant reactions to a detected clinician intervention. The graphs of 3A and 3B represent three phases in the monitoring of the infant stress level. In a first phase 84, a baseline infant motion intensity is determined. Naturally, the infant is a living being and will therefore exhibit some amount of voluntary and involuntary motion. Examples of natural infant motion may include breathing or other spontaneous movements or gestures. In fact, a lack of a minimal threshold level of motion in some embodiments is interpreted as a patient risk factor.

Next, reference 86 indicates increased motion intensity that is associated with a clinician intervention. The clinician intervention into the microenvironment is picked up by the motion sensors of the infant care apparatus and therefore registers as a period of high intensity or high variability motion. As motion detection systems improve, one embodiment further identifies the interaction performed by the clinician with the infant. Such systems may identify the clinician interaction using pattern recognition. This interaction, once identified, may be recorded in an electronic medical record of the infant.

The final phase is the recovery phase 88 wherein the motion intensity graph 82 should return to the baseline motion levels. Once the additional motion intensity detected during the clinician intervention has ended, the motion intensity detected during the recovery phase 88 is due to the motion by the infant. The motion by the infant can be correlated with infant stress levels as described herein. The infant may exhibit stress with a variety of voluntary and involuntary movements.

An infant, even a premature infant, exhibits startle reflexes that are exhibited with facial twitches, particularly of the eyes and mouth. Identification of these facial twitches are an indication of such a startle reaction and increased infant stress. Another stress movement is that of foot bracing, meaning that the infant pushes his legs straight. The infant's hips tend to splay out slightly and push against any kind of bunting or other structure that may be in the vicinity of the feet and legs.

A further movement that is indicative of infant stress is an extension of the infant's arms to the side. Often, a premature infant does not have the energy, muscle strength, or coordination to pull the arms back into a comforting position such as towards the midsagittal plane. When an infant cannot return his arms to this comforting position, the infant may exhibit finger splay by moving the fingers in an extended or separated manner. Thus, finger splay is an additional indication of infant stress level. As noted previously, infant stress level need not only be determined by overall motion intensity. In alternative embodiments, pattern recognition to identify one or more of these noted infant movements may be used to identify the level of stress of the infant.

Referring to FIGS. 3A and 3B, a still further embodiment analyzes both the infant motion intensity as well as changes in physiological parameters of the infant in evaluating the infant's stress level.

In FIG. 3A, it is noted that during the clinician intervention 86, the infant exhibits increased motion intensity combined with a increase in respiration rate 80 and heart rate 78. These increases are combined with a decrease in the SPO2 graph 76. All of these trends are indicative of an increase in infant stress. Because each of these indications coincided with the clinician interaction 86, it can be determined that the interaction itself causes stress to the infant. However, in the recovery phase 88, the motion intensity 82, respiratory rate 80, and the heart rate 78 all decrease and return to the levels found in the baseline phase 84. Similarly, the SPO2 graph 76 continuously increases throughout the recovery phase 88 until the SPO2 graph 76 reaches a pre-intervention level. Therefore, FIG. 3A is an exemplary embodiment of the physiological and motion intensity values that may be observed during a normal or desired stress reaction to a clinician intervention.

The graph of FIG. 3A is compared to that found in FIG. 3B wherein while the infant shows some recovery, particularly in the respiration rate graph 80 during the recovery phase 88, the motion intensity graph 82 remains high after the clinician interaction 86. Similarly, the heart rate graph 78 and the SPO2 graph 76 fail to return to their respective pre-intervention levels during the recovery phase 88. Thus, this stress response found in FIG. 3B is exemplary indicative of an infant that is experiencing increased stress levels after a clinician intervention.

A display of increased infant stress level, as exhibited in FIG. 3B, exemplarily presented using the graphical display 72 of FIG. 2, may prompt a clinician to inspect the infant in order to evaluate the cause of the infant added stress. Such added stress may be from the result of a positioning of the infant or treatment that was started during the clinician intervention. As a non-limiting example, the stress may result from a misplaced IV, catheter, or an accelerated fluid infusion rate.

Figure 4A:
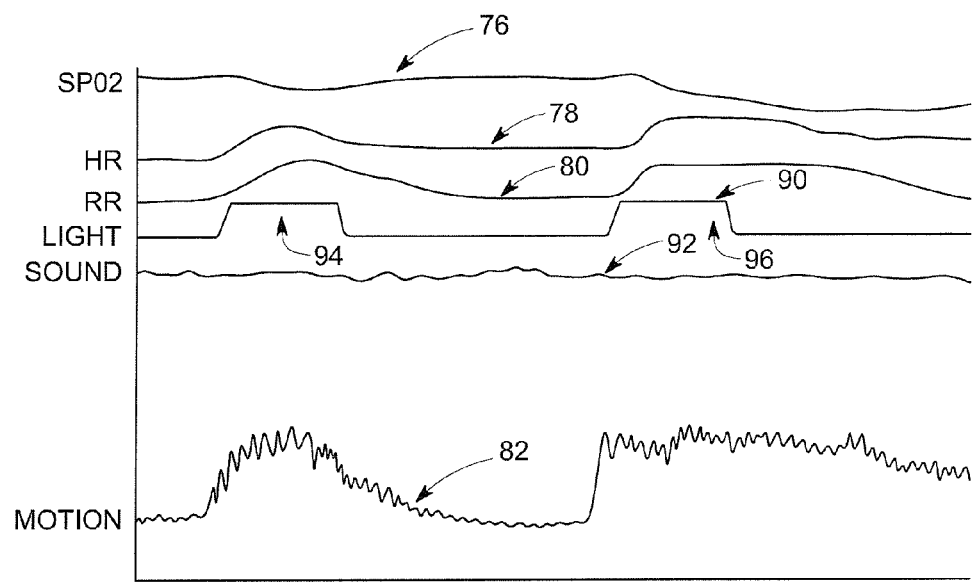
FIGS. 4A and 4B are exemplary graphs of detected motion, physiological parameters, and environmental conditions.
Figure 4B:
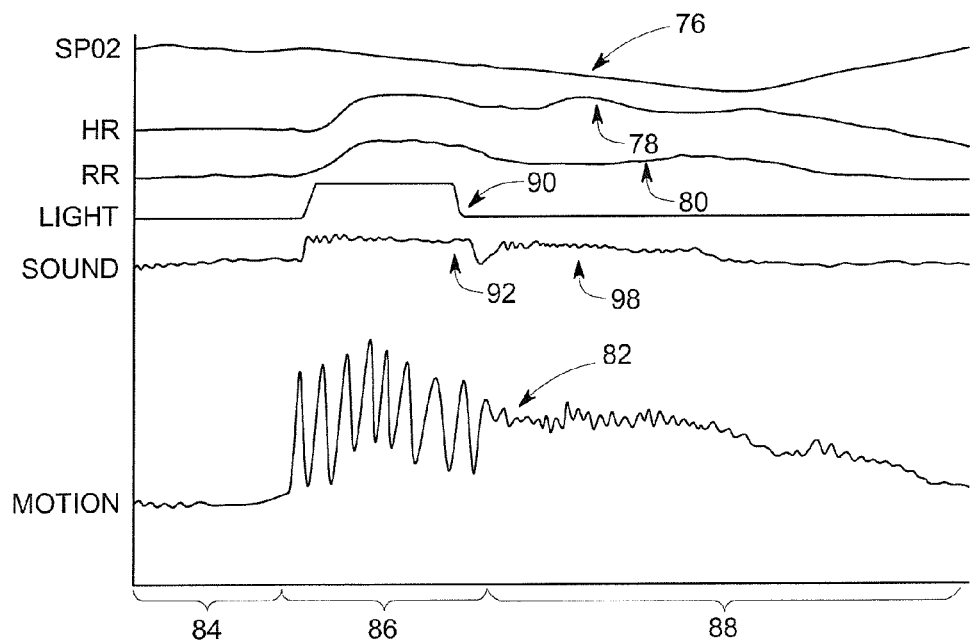

FIGS. 4A and 4B similarly depict exemplary outputs of the signals acquired by the infant care station. It should be noted that like reference numerals between FIGS. 3 and 4 are used to denote like physiological variable graphs. One of the differences between the graphs of FIGS. 3 and 4 are that FIGS. 4A and 4B further include graphs of the environmental condition sensors, namely the light intensity graph 90 and a sound volume graph 92. The graphs of FIGS. 4A and 4B provide exemplary embodiments showing changes in infant motion intensity 82 and an overall increase in stress level in response to changes in environmental conditions.

In FIG. 4A, the light intensity graph 90 shows two periods of increased light intensity. These two periods of increased light intensity may be exemplarily from a clinician entering an NICU and turning on a light in order to interact with one or more of the infants. In the present example, it may be considered that the infant being monitored is not the infant with which the clinician interacted. The detected sound level 92 remains relatively constant throughout the monitored time period.

The infant displays normal or characteristic responses in the motion intensity 82, respiration rate 80, heart rate 78, and SPO2 76 graphs to the increased light intensity of the first period 94. This may indicate a startle reaction or other disturbance to the infant caused by the lights of the NICU turning on. Once the lights are turned off, the infant enters a recovery period and the motion intensity 82, respiration rate 80, heart rate 78, and SPO2 76 all return to previous baseline levels.

At the second period 96 of increased light intensity, the infant does not have the same reaction. To the contrary, even after the external stimuli of the light intensity is removed, the infant's motion intensity 82, respiration rate 80, and heart rate 78 remain elevated, while the infant SPO2 76 remains depressed. These are indications that the infant is experiencing additional or continued stress. The coinciding onsets of the second light period 96 and the infant's adverse reactions results in a correlation between this event and the infant's condition. Therefore, it can be determined that the additional exposure to the light has resulted in stress to the infant, whereas as a previous light exposure did not.

FIG. 4B depicts a still further exemplary embodiment of graphs of conditions monitored by the infant care station. One possible scenario that would cause the graph as depicted in FIG. 4B would be a clinician that interacts with the infant during the clinician's intervention phase 86. In order to interact with the infant, the clinician will enter the NICU and turn on the light, resulting in an increase in the intensity in the light intensity graph 90. Similarly, the interaction between the clinician and the infant may result in increased noise in the NICU which is shown in the sound volume graph 92. Such a procedure may exemplarily be a catheterization, or imaging, or other procedure performed on the infant by the clinician, as would be recognized by one of ordinary skill in the art.

After the interaction between the clinician and the infant ends, the noise from the interaction briefly ceases and the clinician turns off the light in the NICU. Shortly thereafter, the noise level increases again at 98 within the NICU. This exemplarily may be due to crying of one of the other infants in the NICU, or due to the operation or malfunction of a mechanical device within the NICU. A correlation can be identified between the increased noise at 98 and the infant's lack of recovery as identified by the motion intensity graph 82 during the recovery phase 88. In addition to the infant's increased motion intensity, the infant SPO2 76 continues to decrease while the infant's respiratory rate 80 and heart rate 78 remain elevated. Only after the noise 98 ceases, do the infant's measured parameters begin to return to normal. Thus, the exemplary graphs found in FIGS. 3A-4B depict various scenarios of detected infant stress levels.

Figure 5:
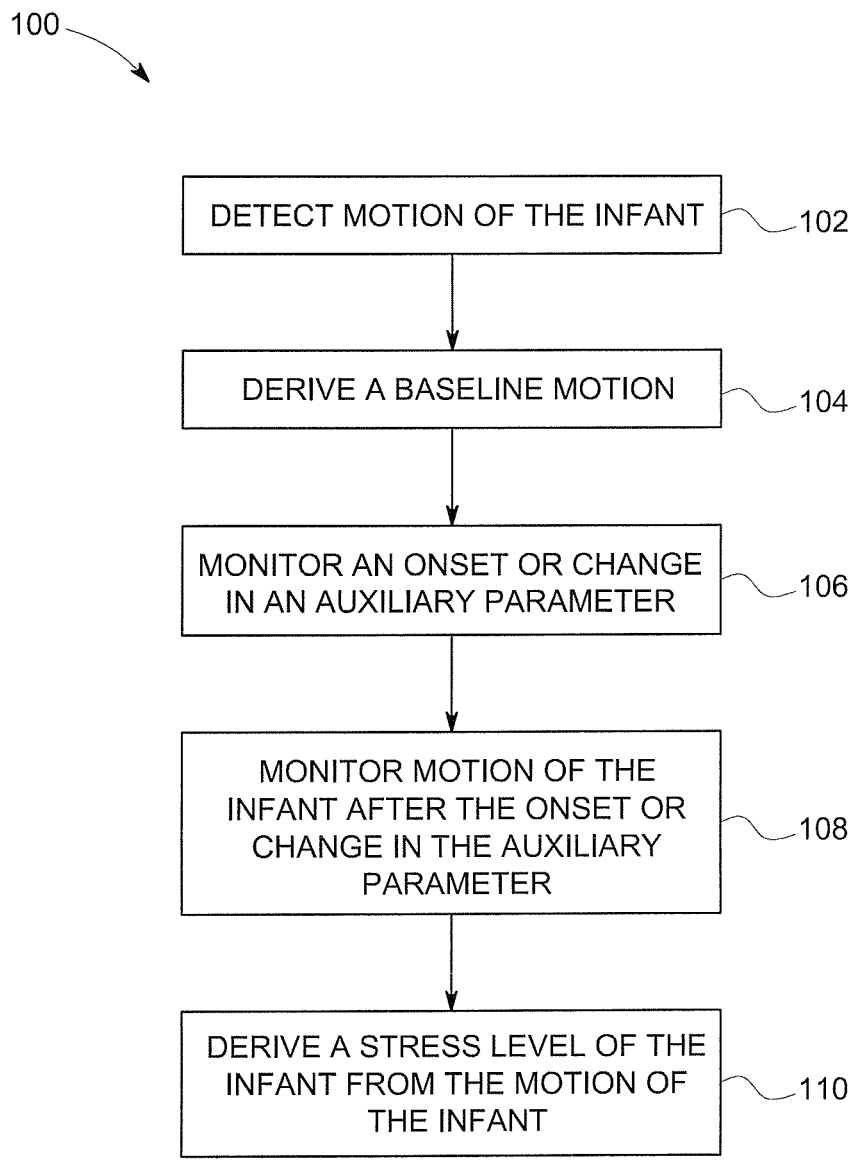
FIG. 5 is a flow chart of an embodiment of a method of monitoring the physiological condition of an infant.

FIG. 5 is a flow chart that depicts an embodiment of a method 100 of monitoring the physiological condition of an infant. The method 100 begins at 102 when motion of the infant is detected. As noted previously with respect to FIGS. 1 and 2, the motion of the infant can be detected in a variety of ways, including video capture or other uses of electromagnetic energization.

At 104, a baseline motion of the infant is derived. As described with respect to FIGS. 3 and 4, the infant will carry out various voluntary and involuntary movements and this will establish a baseline for each individual infant as different infants may exhibit varying degrees of motion in their normal state.

At 106, an onset or change in an auxiliary parameter is monitored. The auxiliary parameter may be any of the parameters that have been described herein, or as would be recognized by one of ordinary skill in the art. The auxiliary parameters may be physiological parameters, such as, but not limited to, SPO2, heart rate, respiratory rate, or blood pressure. Alternatively, the auxiliary parameter may be an environmental condition as described herein such as light intensity or noise volume. Still further examples of the auxiliary parameter may be an indication of a clinician procedure or other interaction, such as a notation found in an electronic medical record of an infant. At 106, one or more of these auxiliary parameters are monitored to detect an onset or change in one or more of these parameters. Examples of onsets of changes in these parameters are exhibited in the examples found in FIGS. 3A-4B.

After an onset or change in an auxiliary parameter is detected at 106, then at 108 the motion of the infant is monitored after the onset or change in the auxiliary parameter. The motion of the infant is detected by the above disclosed motion sensors.

At 110, a stress level of the infant is derived from the monitored motion of the infant. As described above, the infant stress level may be derived by evaluating motion intensity, but may alternatively be derived by evaluating pattern matching to identify particular types of infant motion. Non-limiting examples of particular types of infant motion that are indicative of increased stress include facial twitches, foot bracing, or finger splay. Additionally, as described above with respect to FIGS. 3A-4B, a combination of an evaluation of the infant motion along with one or more of the auxiliary parameters can also be used in order to derive the stress level of the infant. A combination of increased motion intensity along with physiological signs such as increased heart rate or respiration rate, or decreased SPO2, further indicate that the infant is stressed.

Embodiments of the systems and methods as disclosed herein provide an improved indication of infant condition by evaluating a stress level of the infant. Increased stress levels can result in decreased positive outcomes in premature infants. Therefore, clinician interaction and neonate conditions can be improved by monitoring and reporting the infant condition in the manners as described herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of monitoring the physiological condition of an infant within a microenvironment monitored by a plurality of motion sensors, the method comprising:
   detecting motion of the infant with the motion sensors;
   applying pattern matching to the detected infant motion to categorize the detected infant motion;
   deriving a baseline motion intensity for the infant from the detected motion with a processor;
   monitoring an onset or change in at least one auxiliary parameter with an auxiliary sensor;
   monitoring motion intensity of the infant with the motion sensors after the onset or change in the at least one auxiliary parameter; and
   deriving with the processor, a stress level of the infant from the monitored motion intensity of the infant and the categorization of the infant motion.

2. The method of claim 1, further comprising:
   obtaining at least one physiological parameter from the patient with a physiological sensor; and
   obtaining at least one environmental condition of the microenvironment with an environmental sensor.

3. The method of claim 2, wherein the environmental sensor is selected from a light intensity sensor and a sound detector.

4. A system for monitoring a condition of a plurality of infants in an infant care facility, the system comprising:
   a plurality of infant care stations, each infant care station configured for monitoring and treating a neonate infant, wherein each infant care station comprises a microenvironment, a motion sensor disposed about the microenvironment that detects motion of the infant, an environmental sensor that detects an environmental condition of the microenvironment, and a processor that receives the detected motion of the infant and the environmental condition and derives an indication of a stress level of the infant from an intensity of the detected motion;
   a central processor communicatively connected to each of the infant care stations wherein the central processor compares environmental sensor signals from each of the infant care stations and determines a correlation between environmental conditions experienced at each of the infant care stations and corresponding indications of the stress levels of the infants at each of the infant care stations; and
   a graphical display connected to the central processor, the graphical display being operated by the central processor to present an indication of environmental conditions at the infant.

5. A system for monitoring a condition of a plurality of infants in an infant care facility, the system comprising:
   a plurality of infant care stations, each infant care station configured for monitoring and treating a neonate infant, wherein each infant care station comprises a microenvironment, a motion sensor disposed about the microenvironment that detects motion of the infant, an environmental sensor that detects an environmental condition of the microenvironment, and a processor that receives the detected motion of the infant and the environmental condition and derives an indication of a stress level of the infant from an intensity of the detected motion;
   a central processor communicatively connected to each of the infant care stations wherein the central processor compares environmental sensor signals from each of the infant care stations and determines a correlation between environmental conditions experienced at each of the infant care stations and corresponding indications of the stress levels of the infants at each of the infant care stations;
   wherein the central processor identifies common environmental signals across the plurality of infant care stations to identify environmental conditions external to the microenvironments and the central processor identifies a correlation between the infant stress level and the identified environmental conditions external to the microenvironments.

6. The system of claim 5, wherein the environmental sensor is selected from a sound detector, a light intensity sensor, and an ambient temperature sensor.

7. The system of claim 6, wherein each infant care station further comprises at least one physiological sensor that provides an indication of a physiological condition of the infant, the processor of the infant care station processes a physiological signal, a motion signal, and the environmental signals to determine a condition of the infant, the central processor receives the physiological signals and the determinations of the condition of the infants from each of the infant care stations and derives an indication of environmental conditions on the stress level of individual infants independent of the physiological conditions of the infants.

8. The system of claim 5, further comprising a graphical display connected to the central processor, the graphical display being operated by the central processor to present an indication of environmental conditions at the infants.

* * * * *